United States Patent [19]
Kamei

[11] Patent Number: 5,974,163
[45] Date of Patent: Oct. 26, 1999

[54] FINGERPRINT CLASSIFICATION SYSTEM

[75] Inventor: Toshio Kamei, Tokyo, Japan

[73] Assignee: Nec Corporation, Tokyo, Japan

[21] Appl. No.: 08/764,754

[22] Filed: Dec. 12, 1996

[30] Foreign Application Priority Data

Dec. 13, 1995 [JP] Japan ................................. 7-346880

[51] Int. Cl.⁶ .................................................. G06K 9/00
[52] U.S. Cl. ................................... 382/125; 382/228
[58] Field of Search .................... 382/124–127,
382/224, 226–228; 356/71; 340/825.34

[56] References Cited

U.S. PATENT DOCUMENTS

| | | | |
|---|---|---|---|
| 3,988,715 | 10/1976 | Mullan et al. | 382/228 |
| 5,239,594 | 8/1993 | Yoda | 382/224 |
| 5,337,369 | 8/1994 | Shibuya | 382/125 |
| 5,434,932 | 7/1995 | Scott | 382/227 |

FOREIGN PATENT DOCUMENTS

| | | |
|---|---|---|
| 0 516 316 A2 | 5/1992 | European Pat. Off. . |
| 0 651 556 A2 | 4/1994 | European Pat. Off. . |
| 4-52974 | 2/1992 | Japan . |
| 4-52975 | 2/1992 | Japan . |

OTHER PUBLICATIONS

Wilson et al., "Massively Parallel Neural Network Fingerprint Classification System", National Institute of Standards and Technology, NISTIR 4880, pp. 1–66, Jul. 1992.

Aso, "Neural Network Information Processing", Sangyo–Tosho, pp. 40–55 & 198, Jun. 1988.

"Decision Combination in Multiple Classifier Systems", IEEE Transactions on Pattern Analysis and Machine Intelligence, vol. 16, No. 1, Jan. 1, 1994, pp. 66–75.

Primary Examiner—Christopher S. Kelley
Attorney, Agent, or Firm—Foley & Lardner

[57] ABSTRACT

In order to classify fingerprint images with a high precision by integrating classification results and their merits of different classification means making use of their probability data, a fingerprint image classification system of the invention includes: a plurality of classification units (12 and 15), each of the plurality of classification units (12 and 15) generating an individual probability data set (17 or 18) indicating each probability of a fingerprint image (16) to be classified into each of categories; a probability estimation unit (13) for estimating an integrated probability data set (19) from every of the individual probability data set (17 and 18); and a category decision unit (14) for outputting a classification result of the fingerprint image (16) according to the integrated probability data set (19).

2 Claims, 16 Drawing Sheets

- RIDGE LINE
- VALLEY END
- VALLEY LINE

- VALLEY LINE
- RIDGE END
- RIDGE LINE

FIG. 12

$\overbrace{\phantom{xxxxxxxxxxxxxxxxxxxxxxxxxxx}}^{121}$

```
0 0 0     0 0 0
0 1 0     0 1 1   · · ·
0 1 0     0 0 0
```

$\overbrace{\phantom{xxxxxxxxxxxxxxxxxxxxxxxxxxx}}^{122}$

```
0 0 1     1 0 0
0 1 0     0 1 1   · · ·
1 0 1     0 1 0
```

FINGERPRINT CLASSIFICATION SYSTEM

BACKGROUND OF THE INVENTION

The present invention relates to a fingerprint classification system used for automatic classification of fingerprint images.

Fingerprint verification systems are widely used for personal identification. Among them, large systems as that operating in a Police Office are generally provided with a database that has registered within it a large number of fingerprint images classified and sorted to be retrieved efficiently. However, the classification of the large number of fingerprint images involves a large amount of manpower.

Therefore, an automatic fingerprint classification is greatly desired.

As for different methods of fingerprint classification, there is known a method of classification by analyzing features and characteristic lines extracted from thinned images of fingerprints, of which an example is described in a U.S. patent application No. 08/690,744, filed on Aug. 1, 1996, and entitled "Skin Pattern and Fingerprint Classification System", (hereafter to be called the first document), a classification method according to ridge line features of fingerprints, which is disclosed in Japanese patent applications laid open as Provisional Publications No. 52974/'92 and No. 52975/'92 (hereafter called the second and the third documents), or a method of classification making use of a neural network according to a feature vector obtained from fingerprint ridge directions, which is described in "Massively Parallel Neural Network Fingerprint Classification System" by C. L. Wilson et al., National Institute of Standards and Technology, NISTIR 4880, 1992, (hereafter called the fourth document).

In these methods, fingerprints are classified into categories such as the whorl, the loop, the arch and so on.

Each of these fingerprint classification system has its own merits and demerits. For example, the classification method of the first document is sensitive even to a local blot of degraded fingerprint images because it classifies fingerprints according to minutiae of their thinned line images, but has an algorithm that is very insensitive to shifting or rotation of the fingerprint images.

On the contrary, the fingerprint classification method by way of neural network of the fourth document by C. L. Wilson et al. has an algorithm that is insensitive to noises such as local stains or blots, since it classifies fingerprint images making use of features of a whole direction pattern, while it is easy to mis-classify fingerprint images somewhat rotated or shifted.

As described above, different classification methods have different classification characteristics. Therefore, a higher classification performance can be expected by integrating these different fingerprint classification methods.

As for the fingerprint classification system by way of a neural network, the more teaching data sets should bring the higher classification performance. There are cases, however, that even if a large number of teaching data sets can be prepared, it can not learn all of them at once because of its memory limit or restriction of its algorithm.

Also in these cases, the classification precision can be improved by the integration, making use of the large number of teaching data sets as follows. By dividing the large number of teaching data sets into several groups, the data learning is performed for each of the divided groups to obtain each corresponding parameter set. Then, the same unknown fingerprint images are classified by the neural network applying each of the parameter sets. By integrating the classification results thus obtained, a higher precision classification can be expected.

As a method for providing a higher classification performance from classification results obtained from different classification systems or the same classification system with different parameters, it is easily considered to elect a category of a fingerprint to be finally output by a majority from categories such as the arch or the loop indicated by each classification result. For example, in a case where there are provided three different classification systems or a classification system provided with three different parameter sets for classifying a fingerprint image into one of five categories, the plain arch A, the tented arch T, the left loop L, the right loop R and the whorl W, a category indicated by more than one of their three classification results is elected as the final category of the fingerprint image. When the three classification results conflict with each other, the classification result of a system or a parameter set which has shown the most reliable performance is elected, or all of them are rejected, if the rejection is allowed.

Thus, a higher classification precision can be obtained by the integration than each individual classification.

However, with such a simple selection by majority as described above, improvement of classification performance is limited and it is difficult to modify its rejection level, for example, because there is but little variety in the method.

SUMMARY OF THE INVENTION

Therefore, a primary object of the present invention is to provide a fingerprint classification system for classifying fingerprint images with a high precision by integrating merits of different classification methods efficiently, enabling an easy setting of its rejection level at the same time.

In order to achieve the object, a fingerprint classification system of the invention comprises:

a plurality of classification means, each of the plurality of classification means generating an individual probability data set indicating each probability of a fingerprint image to be classified into each of categories referring to a probability table beforehand prepared;

probability estimation means for estimating an integrated probability data set from every of the individual probability data set; and category decision means for outputting a classification result of the fingerprint image according to the integrated probability data set.

So, a fingerprint classification system for classifying fingerprint images is provided in the invention with a high precision by integrating merits of different classification means, enabling an easy setting of its rejection level at the same time.

BRIEF DESCRIPTION OF THE DRAWINGS

The foregoing, further objects, features, and advantages of this invention will become apparent from a consideration of the following description, the appended claims, and the accompanying drawings wherein the same numerals indicate the same or the corresponding parts, and:

FIG. 12 illustrates some example of masking data sets;

DETAILED DESCRIPTION OF THE PREFERRED EMBODIMENTS

Figure 1:
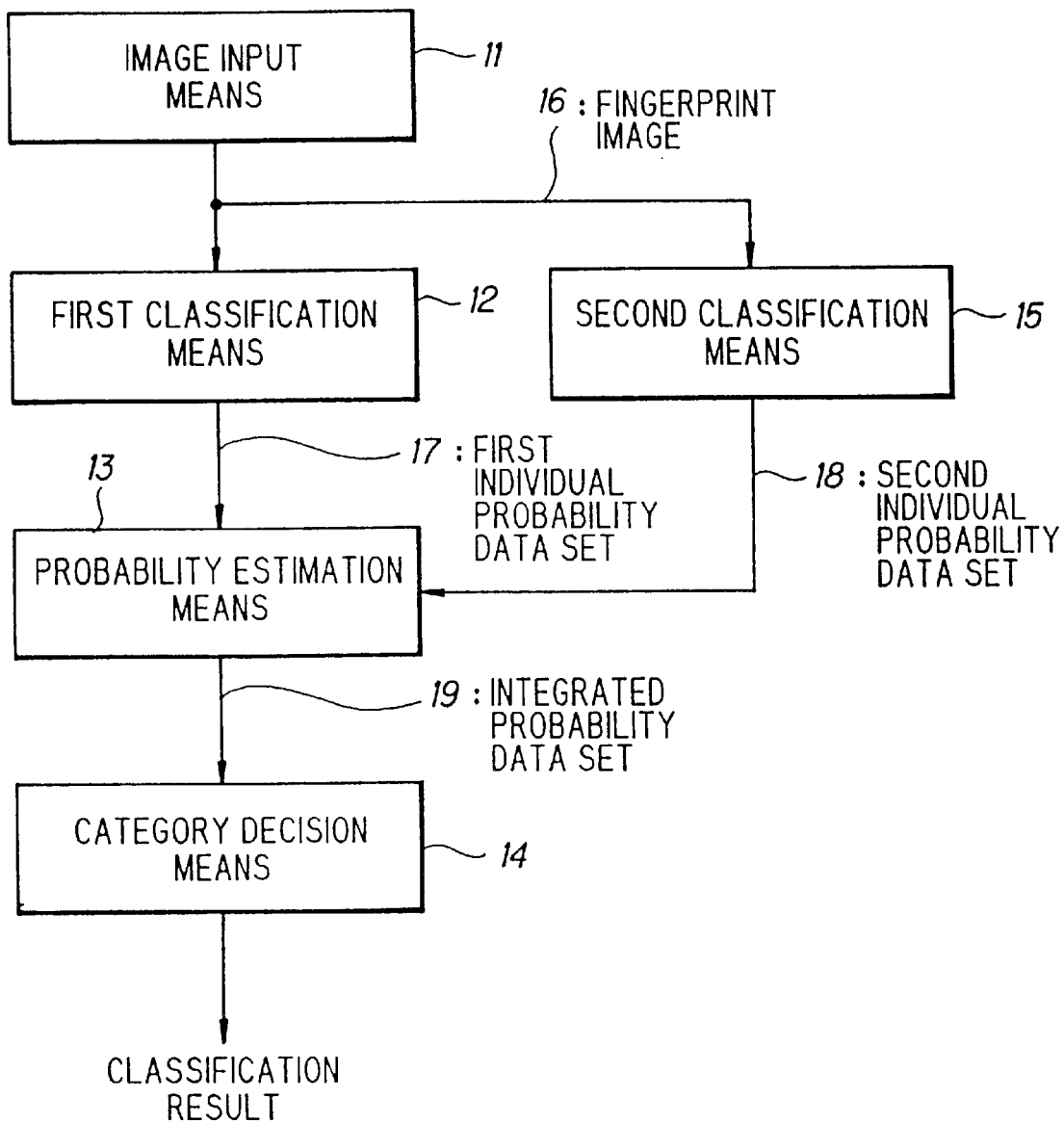
FIG. 1 is a block diagram illustrating an embodiment of fingerprint classification system of the invention.

In the invention, classification results obtained from different classification means or the same classification means with different parameter sets are expressed by probability data, with which probability estimation means estimate each probability of fingerprint images to be classified into each category.

Here, principal of the invention is described in connection with an embodiment, wherein comprised first and second classification means, each for classifying fingerprint images into five categories shown in FIG. 2, that is, the plain arch A, the tented arch T, the right loop R, the left loop L and the whorl W, and probabilities of a fingerprint to be classified into each of the five categries are to be expressed by $P_i(A)$, $P_i(T)$, $P_i(R)$, $P_i(L)$ and $P_i(W)$ respectively, i (i=1, 2) denoting the first or the second classification means.

Suppose a case, for example, that the following two individual probability data sets (1) and (2) are output for a fingerprint image by the first and the second classification means.

$$\begin{aligned} P_1(A) &= 0.01 \\ P_1(T) &= 0.02 \\ P_1(R) &= 0.03 \\ P_1(L) &= 0.04 \\ P_1(W) &= 0.90 \end{aligned} \quad (1)$$

$$\begin{aligned} P_2(A) &= 0.01 \\ P_2(T) &= 0.02 \\ P_2(R) &= 0.03 \\ P_2(L) &= 0.74 \\ P_2(W) &= 0.20 \end{aligned} \quad (2)$$

In the case, the individual probability data set (1), namely, classification result of the first classification means indicates that the first probable candidate of the categries is the whorl W, the second candidate is the left loop L, the third candidate is the right loop R, the fourth candidate is the tented arch T and the last candidate is the plain arch A. On the other hand, the first candidate indicated by the individual probability set (2) of the second classification means is the left loop L, followed by the whorl W, the right loop R, the tented arch T and that plain arch A in the order.

The probability estimation means of the invention calculate integrated probability data set (3) of probabilities $P_0(A)$, $P_0(T)$, $P_0(R)$, $P_0(L)$ and $P_0(W)$ of the fingerprint image to be classified into each of the five categories, by way of the arithmetic means, for example, of these individual probability data sets (1) and (2) as follows.

$$\begin{aligned} P_0(A) &= (0.01+0.01)/2 = 0.01 \\ P_0(T) &= (0.02+0.02)/2 = 0.02 \\ P_0(R) &= (0.03+0.03)/2 = 0.03 \\ P_0(L) &= (0.04+0.74)/2 = 0.39 \\ P_0(W) &= (0.90+0.20)/2 = 0.55 \end{aligned} \quad (3)$$

With the integrated data set (3), the whorl W, the left loop L, the right loop R, the tented arch T and the plain arch A can be nominated as the first to the fifth candidates of the fingerprint to be classified, respectively in that order.

With only that two individual probability data sets (1) and (2) themselves, it is difficult to obtain a definitive classification result specifying the left loop as the first candidate, as the first classification means nominate the whorl W, the left loop L, the right loop R, the tented arch T and the plain arch A, while the second classification means nominating the left loop L, the whorl W, the right loop R, the tented arch T and the plain arch A, from the higher order.

As described above, by allotting a measure of probability to each classification result, the fingerprint classification system of the invention can perform the fingerprint classification with a high precision making use of its statistically significant information.

Furthermore, various modifications can be easily applied in the invention, such as to nominate a second candidate when a sufficient confidence can not be obtained with the first candidate, or to reject the classification result when the sufficient confidence can not be obtained even with the second candidate.

Now, embodiments of the present invention will be described in connection with the drawings.

FIG. 1 is a block diagram illustrating a fingerprint classification system of the invention, comprising;

image input means 11 for generating a fingerprint image 16 of a fingerprint, first and second classification means 12 and 15 for performing a fingerprint classification in a different way and generating a first and a second individual probability data set 17 and 18 indicating each individual probabilities of the fingerprint image 16 to be classified into each classification category, probability estimation means 13 for calculating an integrated probability data set 19 from the first and the second individual probability data sets 17 and 18, and category decision means 14 for deciding and outputting a category or categories as a final classification result of the fingerprint image 16 according to the integrated probability data set 19.

Figure 2:
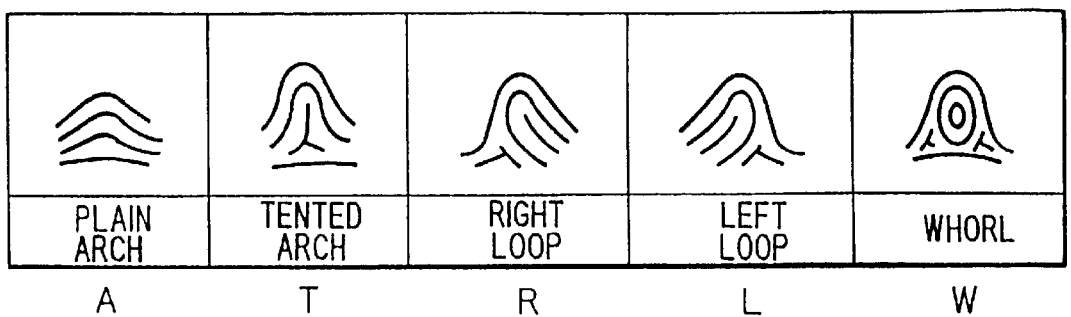
FIG. 2 shows five classification categories, the plain arch A, the tented arch T, the right loop R, the left loop L and the whorl W.

Here, the embodiment is described to classify a fingerprint into the five categories of FIG. 2, the plain arch A, the tented arch T, the right loop R, the left loop L and the whorl W.

The image input means 11 genarate a two-dimensional fingerprint image of 512×512 pixels of 500 DPI, for example, of a fingerprint by way of an image scanner or a CCD camera. The fingerprint image 16 generated by the image input means 11 is supplied to both of the first and the second classification means 12 and 15.

As for the first classification means 12, any appropriate fingerprint classification means can be applied. The embodiment is described to be provided with an apparatus for classifying fingerprints according to their ridge and valley lines and minutiae extracted from thinned line image thereof, such as that described in the first document mentioned beforehand, for example.

The first classification means 12, of which details are to be described afterwards, output the first individual probability data set 17 indicating each probability $P_1(C)$ of the fingerprint image 16 to be classified into each of the five categories, C representing an element of an ensemble of the five categories, the plain arch A, the tented arch T, the right loop R, the left loop L and the whorl W.

As for the second classification means 15, a classification means different from the first classification means 12 is provided, such classification means making use of a neural network as to be also described afterwards, which outputs the second individual probability data set 18, indicating each different individual probabilities $P_2(C)$ of the fingerprint image 16 to be classified into each of the five categories.

As described above, any appropriate classification means can be applied for the two classification means 12 and 15, or more than two classification means may be provided, on condition that they perform fingerprint classification in different way or with different parameter sets with respect to each other.

The probability estimation means 13 calculates the integrated probability data set 19 indicating each integrated probability $P_0(C)$ of the fingerprint image 16 to be classified into each of the five categories for delivering to the category decision means 14, from the individual probabilities $P_1(C)$ and $P_2(C)$ of the first and the second individual probability data sets 17 and 18.

The integrated probability $P_0(C)$ may be calculated by an arithmetic mean according to the following equation.

$$P_0(C)=(P_1(C)+P_2(C))/2$$

Instead of the above arithmetic mean, a normalized geometric mean may be calculated for the integrated probability $P_0(C)$ as follows.

$$P_0(C) = (P_1(C) \times P_2(C))^{1/2} \Big/ \sum_C (P_1(C) \times P_2(C))^{1/2}$$

The category decision means 14 decides caregories $C_0$ to be output according to the integrated probability data set 19.

In case a first candidate is to be output without rejection, a category Co represented by following equation is output.

$$C_0 = \mathrm{argmax}_C P_0(C),$$

indicating a category which gives the highest value of the integrated probability $P_0(C)$ among the five categories.

In case the first candidate having a confidence more than a rejection level t is to be output, the category $C_0$ of the above equation is output when the maximum integrated probability $P_0(C_0) \geq t$ and otherwise the classification result is rejected. Taking the example of the integrated data set (3) referred to beforehand, when the rejection level t is set to 0.5, the whorl W is output nominated as the first candidate, which is rejected by setting the rejection level t to 0.9 for reserving higher classification precision.

In case a second candidate is requested to be added when sufficient confidence is not obtained with the first candidate, on condition it gives a certain confidence, the following processes are performed there. Each category C is ranged in descending order of its integrated probability $P_0(C)$ from the first to the fifth candidate. When the first candidate shows its integrated probability $P_0(C)$ more than a rejection level $t_1$ provided for single nomination, solely the first candidate is output. Otherwise, the first and the second candidates are output on condition that the sum of their integrated probabilities $P_0(C)$ attains a rejection level $t_2 \geq t_1$ provided for double nomination. And if not, the fingerprint is rejected to be unclassified.

In the example of the integrated data set (3), only the whorl W is output as the first candidate by setting the rejection level as $t_1=t_2=0.5$. When they are set as $t_1=t_2=0.9$ for reducing mis-classification rate, also the left loop L is output as the second candidate in addition to the first candidate of the whorl W. Also, the integrated data set (3) is rejected when the rejection level is set as $t_1=t_2=0.95$ for avoiding errors in an automatic classifcation.

Thus, a fingerprint classification system for classifying fingerprint images with a high precision is provided in the invention by integrating merits of different classification methods efficiently, enabling an easy setting of its rejection level at the same time.

In the following paragraphs, some concrete examples of classification means to be applied for the first and the second classification means 12 and 15 are described, which may be through any appropriate classification means as described beforehand.

For the first, an example of the classification means 12 is described, wherein a fingerprint classification system described in the first document is applied.

Fingertip patterns are generally composed of raised parts called ridges of the outer skin and lowered parts called valleys between the ridges. The ridges and the valleys of the outer skin form a striped pattern, which can be roughly classified into three groups.

Figure 3A:
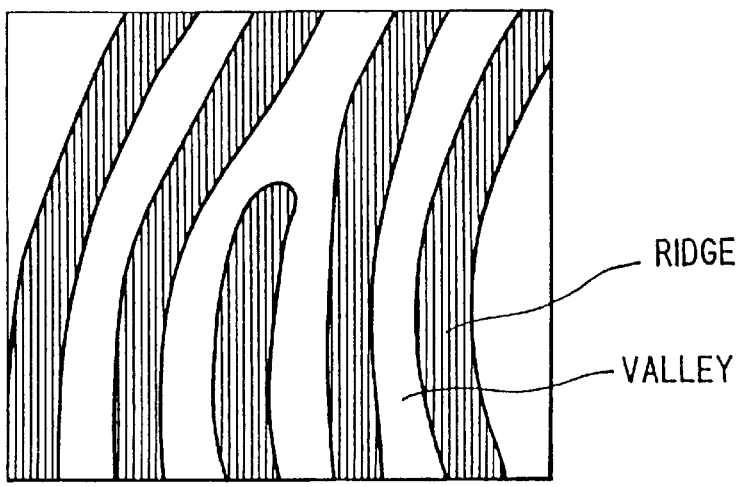
FIG. 3A is a magnified image of an example of a fingerprint image having a pair of minutiae.
Figure 3B:
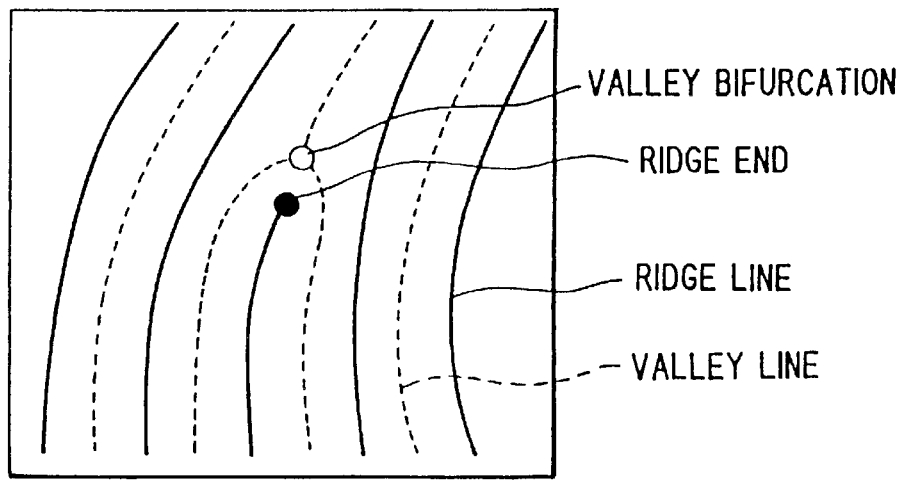
FIG. 3B is a graphic chart illustrating a line image of the magnified image of FIG. 3A.
Figure 4A:
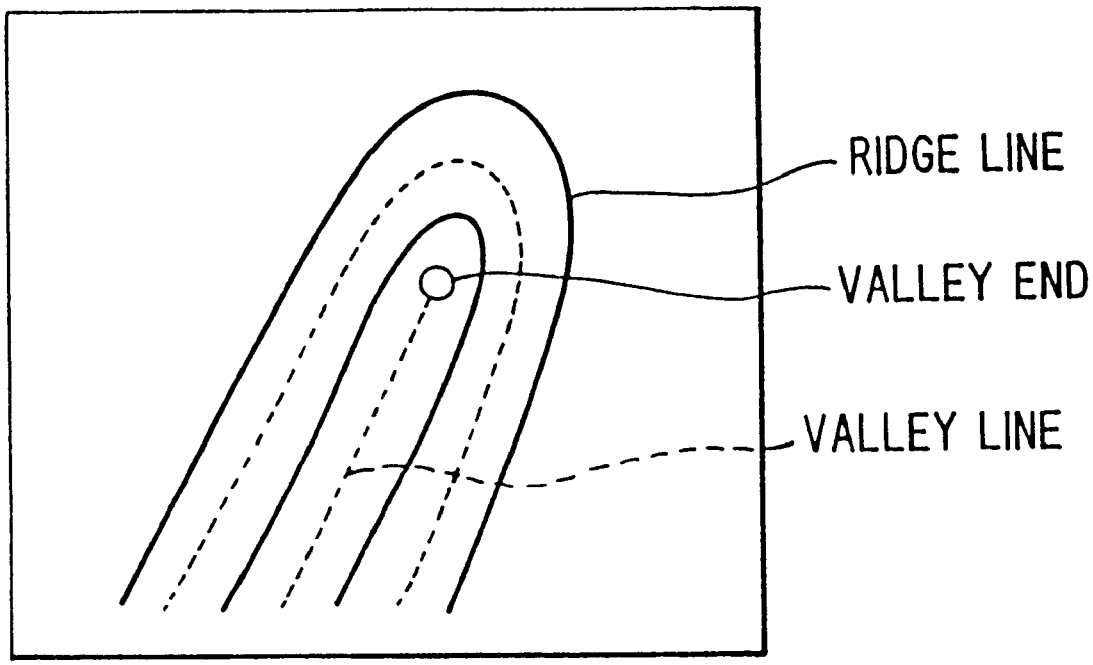
FIG. 4A is a graphic chart illustrating a line image of semicircle stripes of ridges surrounding a valley end.
Figure 4B:
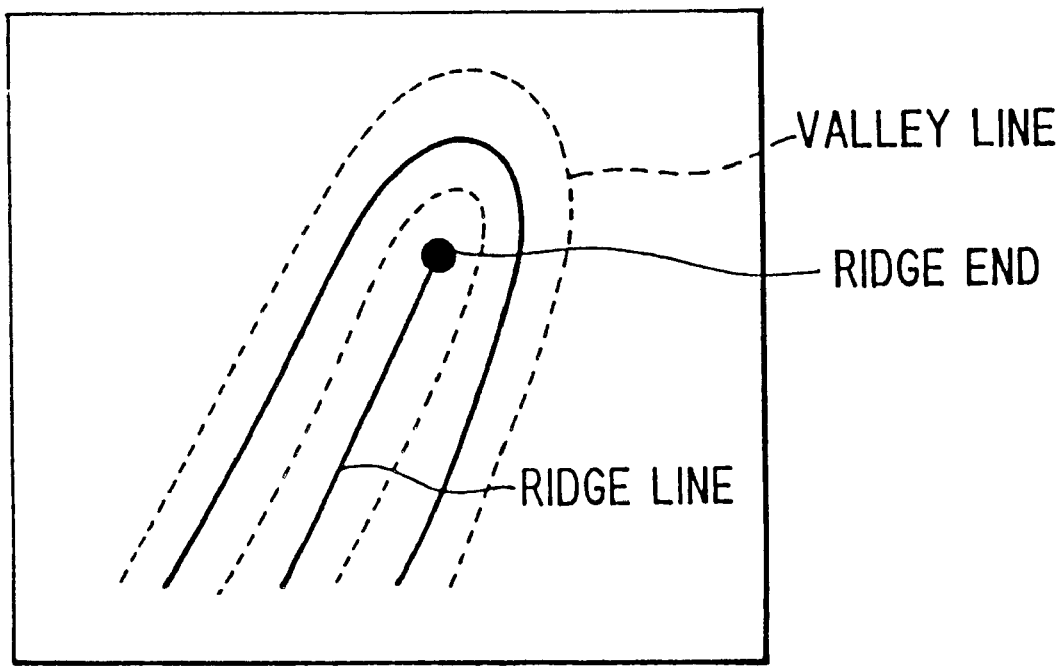
FIG. 4B is a graphic chart illustrating another line image of semicircle stripes of valleys surrounding a ridge end.
Figure 5A:
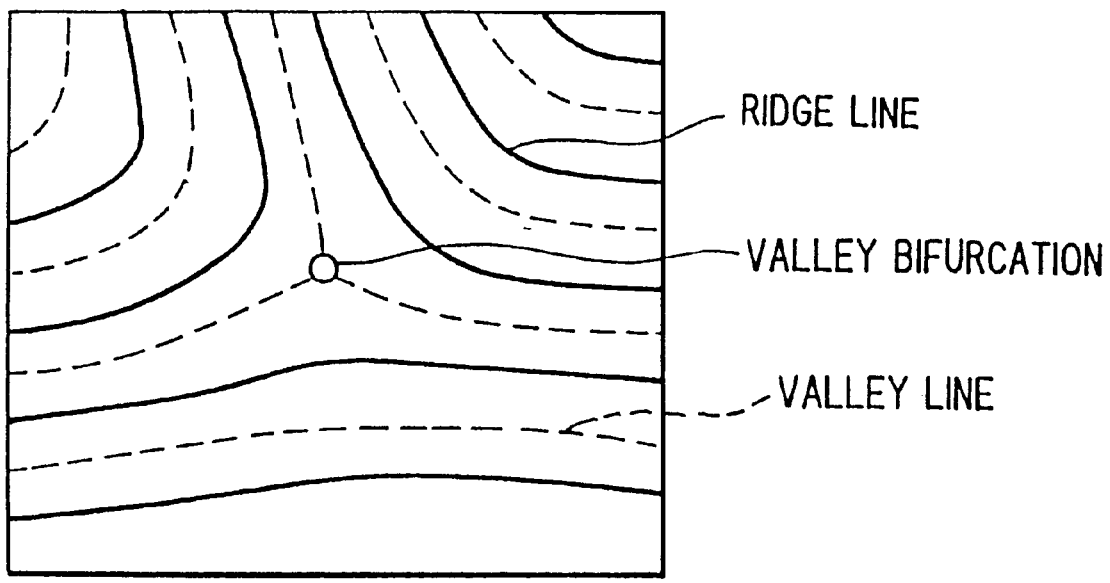
FIG. 5A is a line image illustrating an example of delta stripes surrounding a valley bifurcation.
Figure 5B:
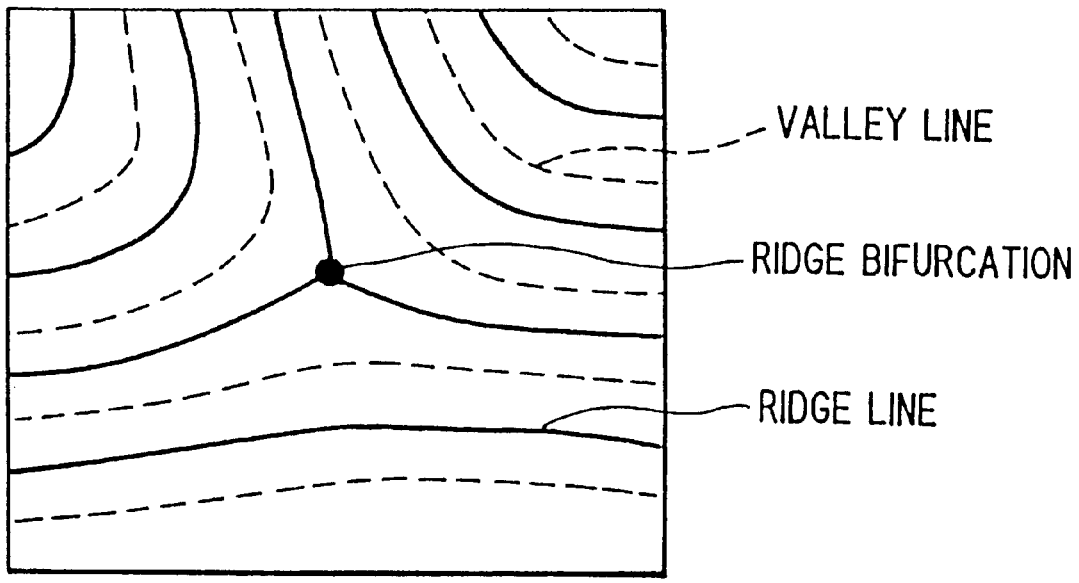
FIG. 5B is a line image illustrating another example of delta stripes surrounding a ridge bifurcation.

FIG. 3A is a magnified image of an example of a first group, wherein ridges and valleys are ranged in parallel and a ridge end and a valley bifurcation are comprised as shown in FIG. 3B illustrating a line image of FIG. 3A for expressing line structure of the striped pattern. Examples of a second group are shown in FIG. 4A and FIG. 4B, each illustrating a line image of semicircle stripes of ridges and valleys surrounding a valley end or a ridge end respectively. FIG. 5A and FIG. 5B are also line images illustrating examples of the third group composed of delta stripes surrounding a valley bifurcation or a ridge bifurcation respectively.

Among the three groups, semicircle stripe patterns of the second group are peculiar patterns found at parts called, in criminal laboratories, as Cores of fingerprints and regarded as an important feature for fingerprint classification together with delta stripe patterns of the third group found at parts called Deltas of fingerprints.

In the first classification means 12 of FIG. 1, singular points in these peculiar patterns are extracted for classifying fingerprints according thereto.

Now, extraction of the singular point is described first.

End points or bifurcation points of ridges or valleys (hereafter called generically as minutiae) are to be found usually coupled with another minutia in patterns of parallel stripe of the first group as shown in FIG. 3B, for example. That is, a valley bifurcation is found corresponding to a ridge end, while a ridge bifurcation is found corresponding to a valley end. Therefore, it can be said that there is a dual correspondence in each two minutiae in the parallel stripe pattern.

On the other hand, in the semicircle stripe patterns as shown in FIG. 4A or FIG. 4B, and in the delta stripe patterns as shown in FIG. 5A or FIG. 5B, where directions of ridges or valleys vary sharply, any minutia has no corresponding minutia. Hereafter, such minutia having no corresponding minutia is called a singular point, and a singular point found in a semicircle stripe pattern is called a core type singular point and that in a delta stripe pattern is called a delta type singular point.

In the first classification means 12, singular points, namely minutiae without corresponding minutia are detected at a first step, by searching and omitting minutiae having dual correspondence.

Almost every one of the singular points is found either in the Cores or the Deltas. Therefore, only by counting the number of singular points of a fingerprint, the fingerprint can be classified with a certain exactitude, when it is sufficient for the fingerprint to be classified into one of three categories of the arch, the loop and the whorl.

Therefore, in the first classification means 12, characteristic ridge lines or valley lines (hereafter called characteristic lines) around the singular point are found and traced for extracting features of the fingerprint to discriminate a category of the fingerprint to be classified into according thereto.

Suppose that fingerprints are to be classified into the five categories of FIG. 2, the plain arch A, the tented arch T, the right loop R, the left loop L and the whorl W. In this case, numbers of the core type singular points to be found in a fingerprint of each of the five categories, the plain arch A, the tented arch T, the right loop R, the left loop L and the whorl W, are 0, 1, 1, 1 and 2 respectively.

Although the same numbers of the delta type singular points are to be found there too, they are sometimes difficult to be detected because fingerprints sufficiently wide for containing the delta type singular point can be rarely gathered in actual cases. For that reason, the example of the classification means 12 is described here in connection with a case where the core type singular point is made use of.

Among fingerprints to be classified into the Loop type (the right loop R and the left loop L) and the tented arch T, there are many fingerprints which are similar to each other and difficult to be classified into either of the two types. The difference between the two types must be discriminated by detecting whether a loop line can be found there or not. The reason is that the characteristic feature of the tented arch T lies in that fingerprints of the type composed of arch lines have no loop line, while fingerprints of the Loop type comprise loop lines.

Figure 6:
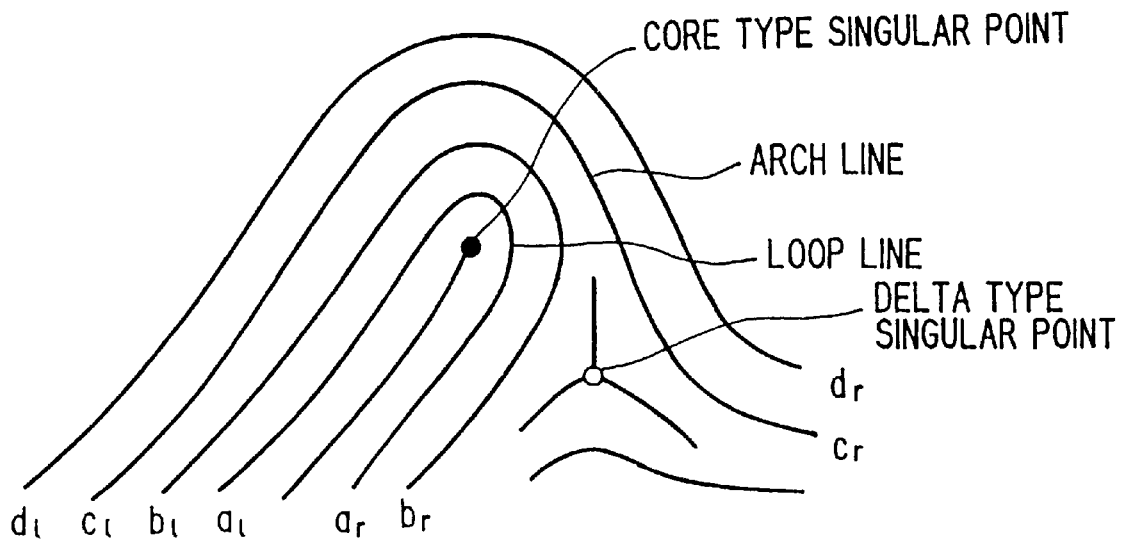
FIG. 6 illustrates an example of a fingerprint of the left loop L.

Here, a loop line means a horseshoe shaped line of which both ends flow to the same side from top of the horseshoe shape, to right side in the right loop R and to left side in the left loop L, as a line $a_l$ to $a_r$ or $b_l$ to $b_r$ of FIG. 6 illustrating an example of a fingerprint of the left loop L. On the other hand, an arch line means an arch shaped line of which each end flows to each other side from top of the arch shape, as a line $c_l$ to $c_r$ or $d_l$ to $d_r$ of FIG. 6. When there is an imperfection as a gap on a ridge line or a valley line, as is general, the ends of the line should be traced properly compensating the discontinuity of the line for discriminating its line type.

Figure 7:
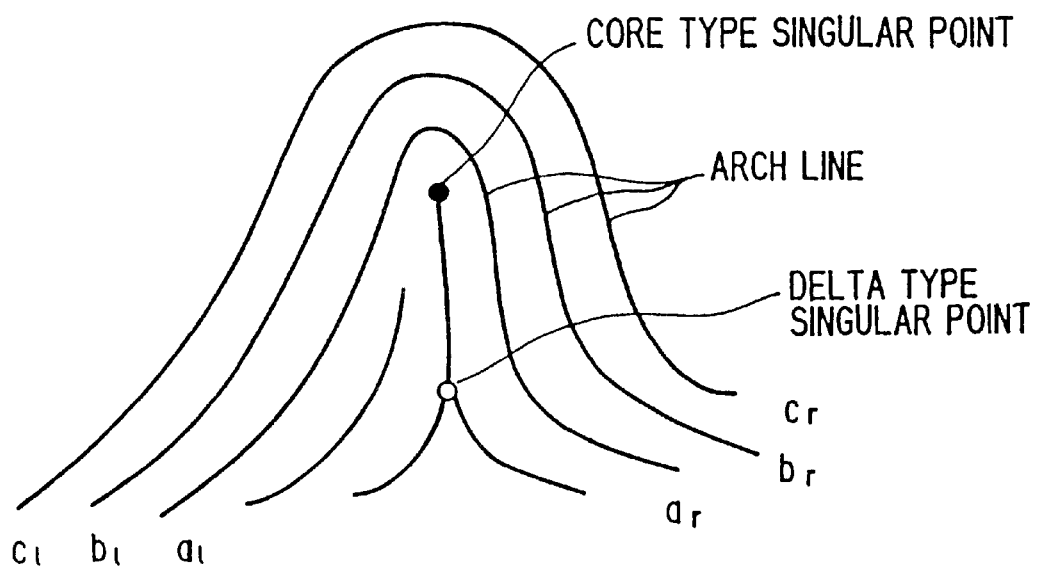
FIG. 7 illustrates an example of a fingerprint of the tented arch T.

In the Loop type, the core type singular point is surrounded by horseshoe part of a loop line as shown in FIG. 6, while it is surrounded by top part of an arch line in fingerprints of the tented arch T as shown in FIG. 7.

Therefore, it can be said that the difference between the Loop type and the tented arch T can be discriminated by detecting whether the nearest line surrounding the core type singular point is a loop line or an arch line.

Figure 8A:
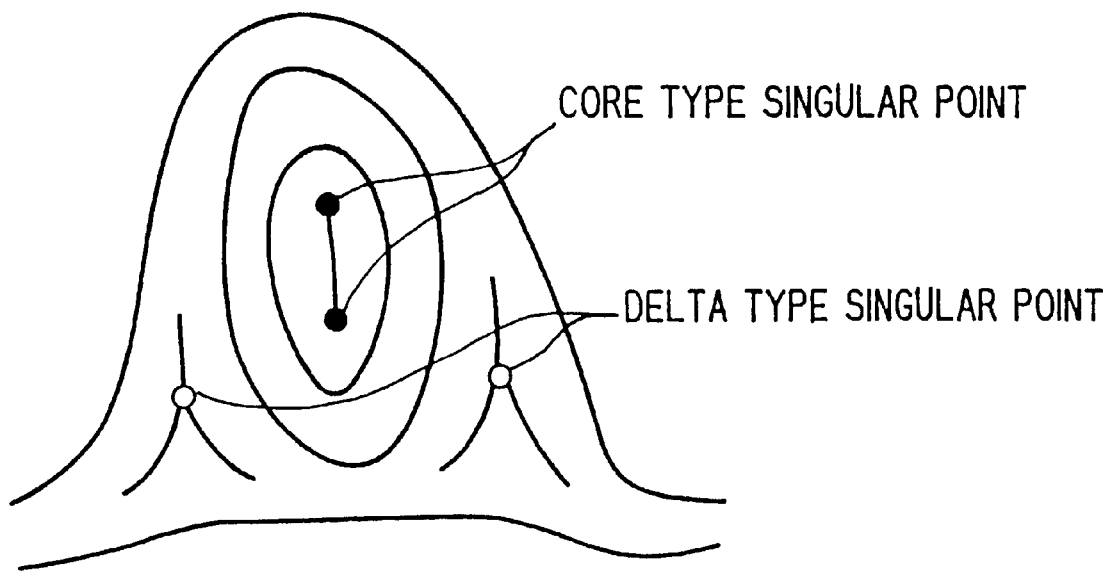
FIG. 8A illustrates an example of a fingerprint of the whorl W.
Figure 8B:
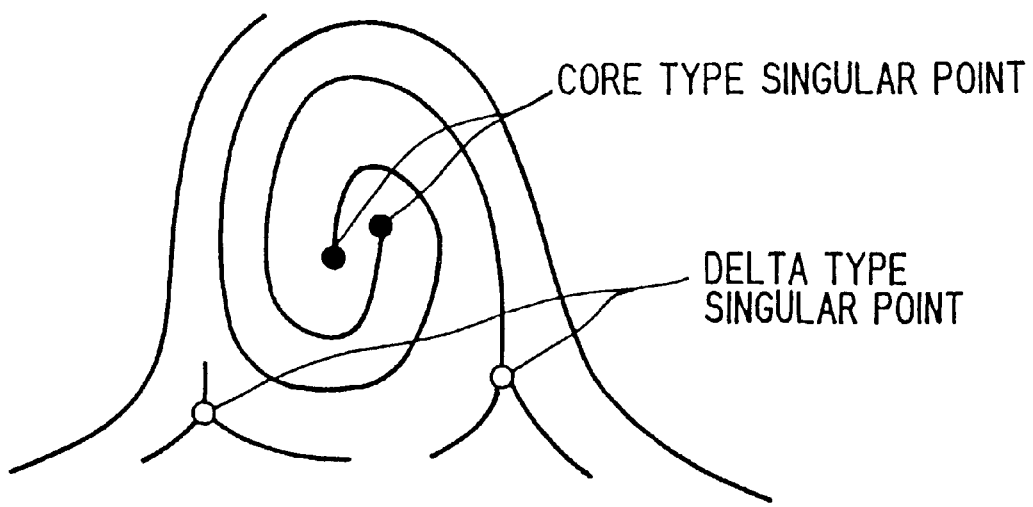
FIG. 8B illustrates another example of a fingerprint of the whorl W.

As for fingerprints of the whorl W having two core type singular points, line flow around the two core type singular points can be classified into two categories as shown in FIG. 8A and FIG. 8B illustrating each example of the two categories of the whorl W. In FIG. 8A, the two core type singular points are connected by a ridge line or a valley line and surrounded by a circular line. In the other category of FIG. 8B, two whorl lines are flowing out of the two core type singular points.

Figure 9:
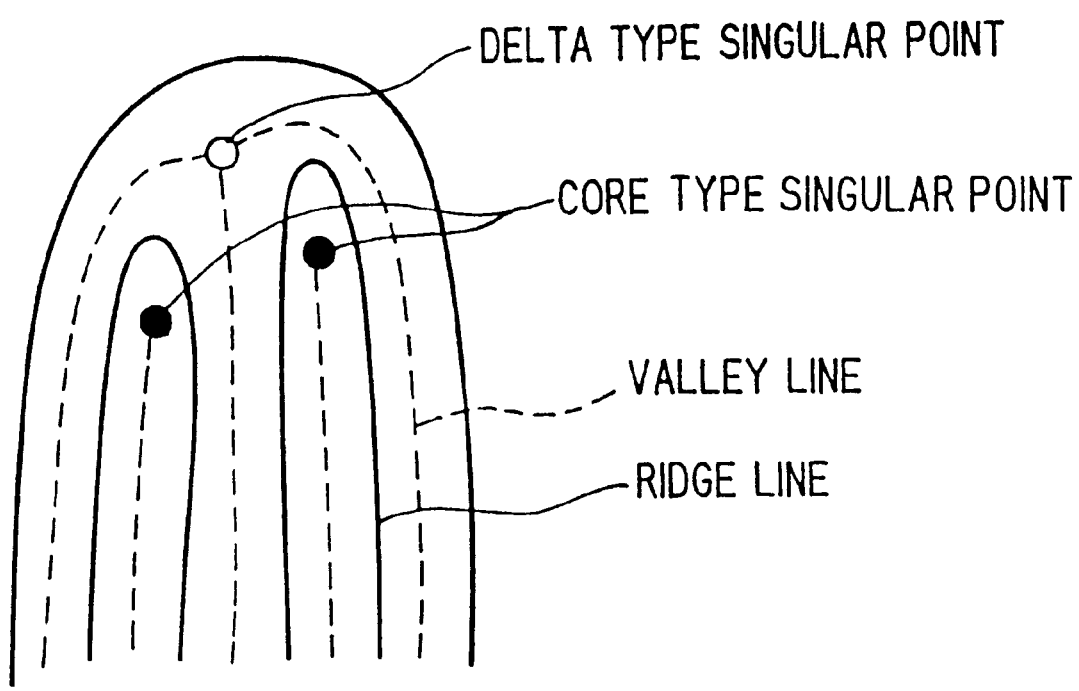
FIG. 9 shows a Loop type fingerprint having two loop lines.

Therefore, by checking a characteristic line or characteristic lines connected to the core type singular points, fingerprints to be classified into other than the whorl W in spite of having two core type singular points, a Loop type fingerprint having two core type singular points as shown in FIG. 9 for example, can be discriminated, preventing wrong classification into the whorl W.

Figure 10:
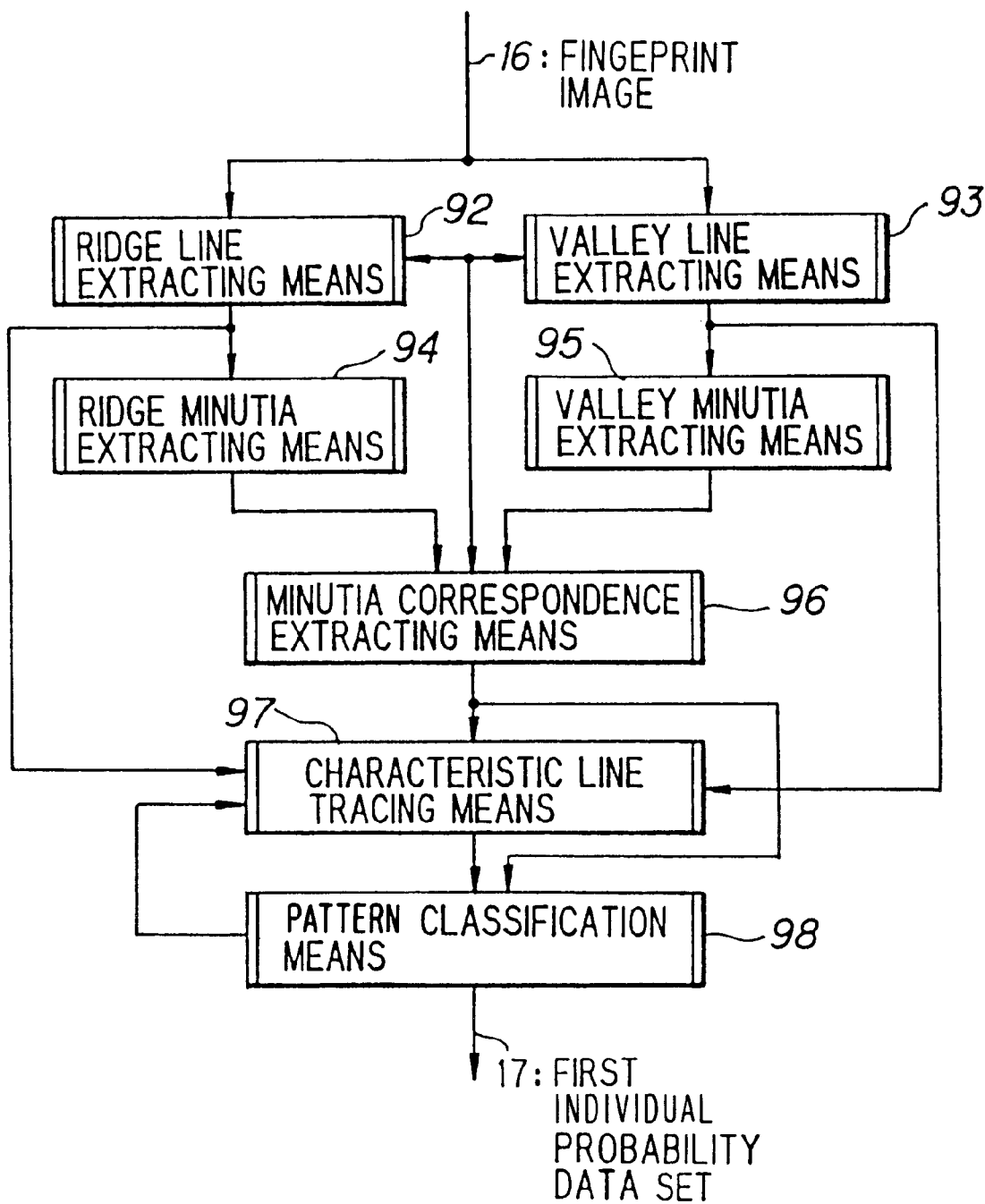
FIG. 10 is a block diagram illustrating a basic configuration of an example of the first classification means 12 of FIG. 1.

FIG. 10 is a block diagram illustrating a basic configuration of the first classification means 12 of FIG. 1, wherein are comprised;

ridge line extracting means 92 for extracting ridge line data corresponding to ridges of the skin pattern from the fingerprint image 16 of FIG. 1, valley line extracting means 93 for extracting valley line data corresponding to valleys of the skin pattern from the fingerprint image 16, ridge minutia extracting means 94 for extracting ridge minutiae from the ridge line data, valley minutia extracting means 95 for extracting valley minutiae from the valley line data, minutia correspondence extracting means 96 for extracting minutia correspondence information by detecting dual correspondence among the ridge minutiae and the valley minutiae, from the ridge line data, the valley line data, the ridge minutiae and the valley minutiae, characteristic line tracing means 97 for extracting features of characteristic lines of the skin pattern by finding and tracing the characteristic lines referring to the minutia correspondence information, the ridge line data and the valley line data, and pattern classification means 98 for classifying the fingerprint image 16 according to the features of characteristic lines and the minutia correspondence information.

Figure 11:
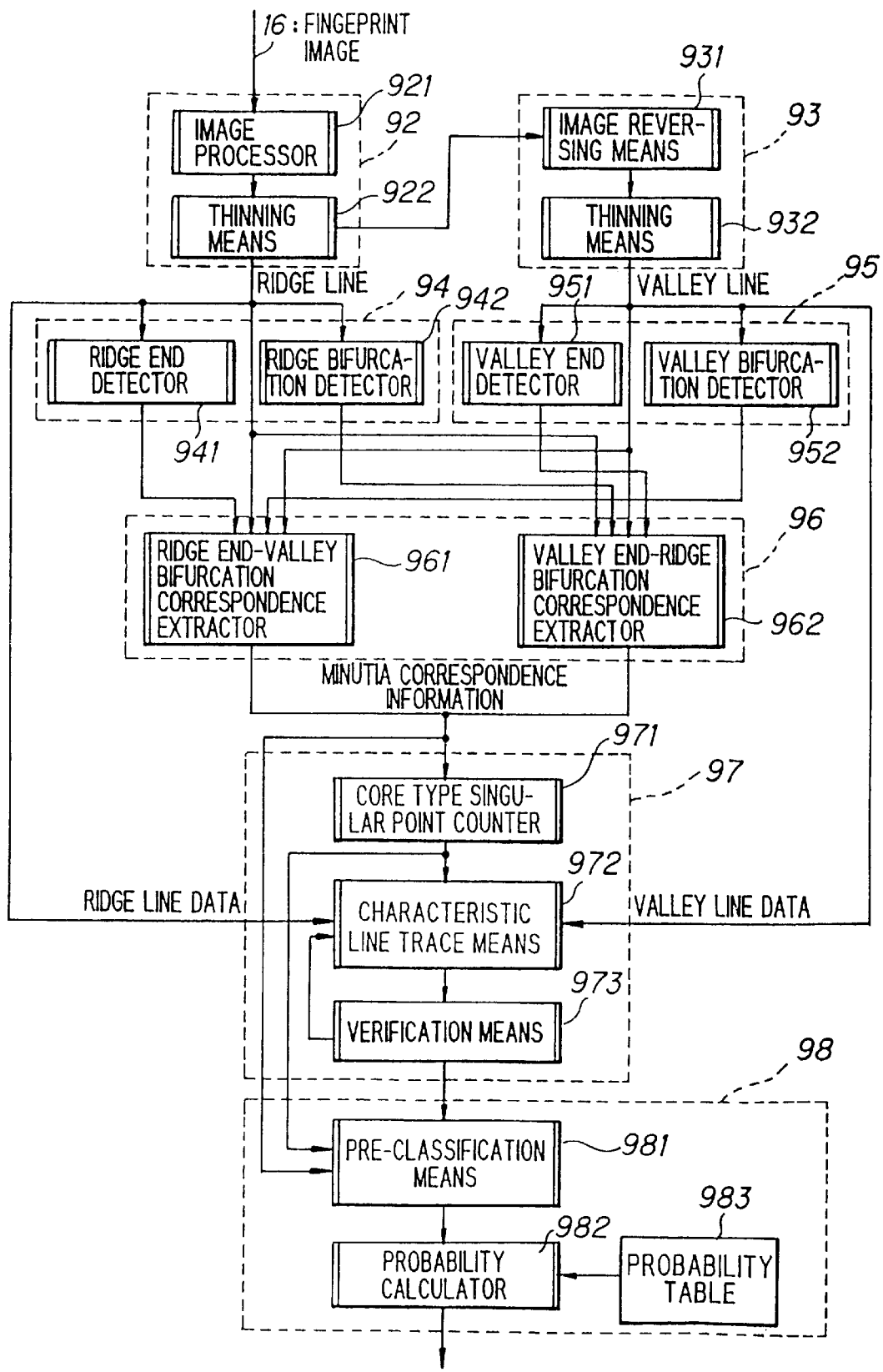
FIG. 11 is a more detailed block diagram illustrating the example of classification means of FIG. 10.

FIG. 11 is a more detailed block diagram illustrating details of the example of classification means of FIG. 10.

The ridge line extracting means 92 is provided with an image processor 921 for obtaining binary image data from the fingerprint image 16 supplied through the image input means 11 of FIG. 1 and thinning means 922 for extracting the ridge line data from the binary image data. The valley line extracting means 93 is provided with image reversing means 931 for obtaining reversed image data of the ridge line data and thinning means 932 for extracting the valley line data from the reversed image data of the ridge line data.

The ridge minutia extracting means 94 has a ridge end detector 941 and a ridge bifurcation detector 942 for detecting and listing up ridge ends and ridge bifurcations, while the valley minutia extracting means 95; has a valley end detector 951 and a valley bifurcation detector 952 for detecting and listing up valley ends and valley bifurcations.

The ridge line data, and the valley line data after processes in the thinning means 922 or 932, are thinned line bit maps. For detecting minutiae from the thinned line bit maps, there are prepared masking data sets, some examples of which are illustrated in FIG. 12. Thinned line bit maps of the ridge line data and the valley line data are scanned and compared with each of the masking data sets of 3×3 bits. When any 3×3 bits of the thinned line bit maps coincides with any of the masking data sets, a center point of the 3×3 bits is defined as a minutia. Minutiae corresponding to one of the masking data sets of 121 of FIG. 12 are end points and those of 122 are bifurcations.

Thus, the ridge minutia extracting means 94 and the valley minutia extracting means 95 extract ridge ends, ridge bifurcations, valley ends and valley bifurcations from the ridge line data and the valley line data, and output a minutia list registered of minutia information as their coordinates, kind, etc.

The minutia correspondence extracting means 96 has a ridge end—valley bifurcation correspondence extractor 961 and a valley end—ridge bifurcation correspondence extractor 962 for searching dual correspondence of the ridge ends to the valley bifurcations and those of the valley ends to the ridge bifurcations referring to the ridge line data and the valley line data and for outputting the minutia correspondence information for every of the minutiae, that is, information concerning its paired minutia if it has a corresponding minutia, or its state of singularity if it has no correspondence, together with its coordinates, its kind (end or bifurcation point of ridge or valley line), its connected line, positional information between the connected line and the paired minutia, and so on.

The characteristic line tracing means 97 has a core type singular point counter 971 for counting up number of core type singular points based on the minutia correspondence information, characteristic line trace means 972 for finding and tracing characteristic lines around the core type singular points according to number of the core type singular points referring to the ridge line data and the valley line data, and verification means 973 for verifying features extracted from the characteristic lines.

Here, the characteristic line trace means 972 performs the trace of characteristic lines assuming the fingerprint image 16 is a whorl W when it has two core type singular points, or assuming that it is a tented arch T or a Loop when it has one core type singular point. The verification means 973 is provided for dealing with mis-traces of the characteristic lines, because a correct tracing is not always guaranteed due to the effects of noises imposed therein.

The pattern classification means 98 is equipped with pre-classification means 981 for pre-classifying the skin pattern into detailed categories according to the minutia correspondence information delivered from the minutia correspondence extracting means 96, the number of core type singular points counted by the characteristic line tracing means 97 and the features of the characteristic lines verified there, and a probability calculator 982 for classifying the fingerprint image 16 into one of the five output categories referring to a probability table 983 indicating each probability to be classified into each of the output categories of fingerprint images pre-classified into each of the detailed categories.

Now, processes in the pattern classification means 98 are described.

The pre-classification means 981 first classifies the fingerprint image 16 temporarily into one of six categories, the plain arch A, the tented arch T, the right loop R, the left loop L, the whorl W, and unknown X. Here, the whorl W corresponds to fingerprints detected to have two singular points surrounded with characteristic lines, the left loop L to those having one singular point with a nearest surrounding line of the Left Loop, the right loop R to those having one singular point with a nearest surrounding line of the Right Loop, the tented arch T to those having one singular point surrounded by an arch line, the plain arch A to those having no core type singular point, and the unknown X corresponds to fingerprint images rejected by the verification means 973.

Then, the pre-classification means 981 also classifies the fingerprint image 16 according to its number of core type singular points into one of four categories, for example, each having 0, 1, 2, or more than 2 core type singular points. Thus, the pre-classification means 981 classifies the fingerprint image 16 into one of 24 detailed categories expressed as $c_i$ (i=1, . . . , 24), namely, the six categories of the plain arch A to the unknown X multiplied by four categories of 0 to more than 2 singular points. Considering also the number of delta type singular points, 0, 1, 2 and more than 2, for example, the pre-classification may be performed into one of 64=6×4×4 detailed categories.

For each detailed category $c_i$, five probabilities $P_{ji}$ are prepared in the probability table 983, j being one of symbols A, T, L, R or W, each representing one of the five categories $C_j$, the plain arch A, the tented arch T, the left loop L, the right loop R and the whorl W, respectively. The probabilities $P_{ji}$, which represents probability of a fingerprint in a detailed category $c_i$ to be finally classified into a category $C_j$, can be obtained from a sufficient number of learning data as follows.

When a number of learning data already classified, by manual for example, into one of the five categories $C_j$ are pre-classified by the pre-classification means 981 into detailed categories ci, the probability $P_{ji}$ is calculated according to following equation.

$$P_{ji} = N_{ji} \bigg/ \sum_k N_{ki}$$

where $N_{ki}$ represents number of learning data already classified into a category $C_k$ of the five categories and pre-classified into a detailed category $c_i$.

When each number of patterns of the plain arch A, the tented arch T, the left loop L, the right loop R and the whorl W pre-classified into a detailed category $c_i$ is 3, 5, 89, 1, and 2 respectively, then the probabilities $P_{Ai}$, $P_{Ti}$, $P_{Li}$, $P_{Ri}$ and $P_{Wi}$ are 3%, 5%, 89%, 1% and 2% respectively.

About 10,000 cases of learning data will provide a probability table sufficiently precise. Returning to FIG. 11, the probability calculator 982 allots to the fingerprint 16 with five probability values $P_{Ai}$, $P_{Ti}$, $P_{Li}$, $P_{Ri}$ and $P_{Wi}$ corresponding to a detailed category $c_i$ where the fingerprint image 16 is pre-classified, as the individual probabilities $P_1(C)$.

Thus, the first individual probability data set 17 of FIG. 1 is obtained by the first classification means 12.

Heretofore, a fingerprint classification system of the first document is described as an example to be applied for the first classification means 12 of FIG. 1 for obtaining the first individual probability data 17.

Now, another example of the fingerprint classification means to be applied for the second classification means 15 is described.

Figure 13:
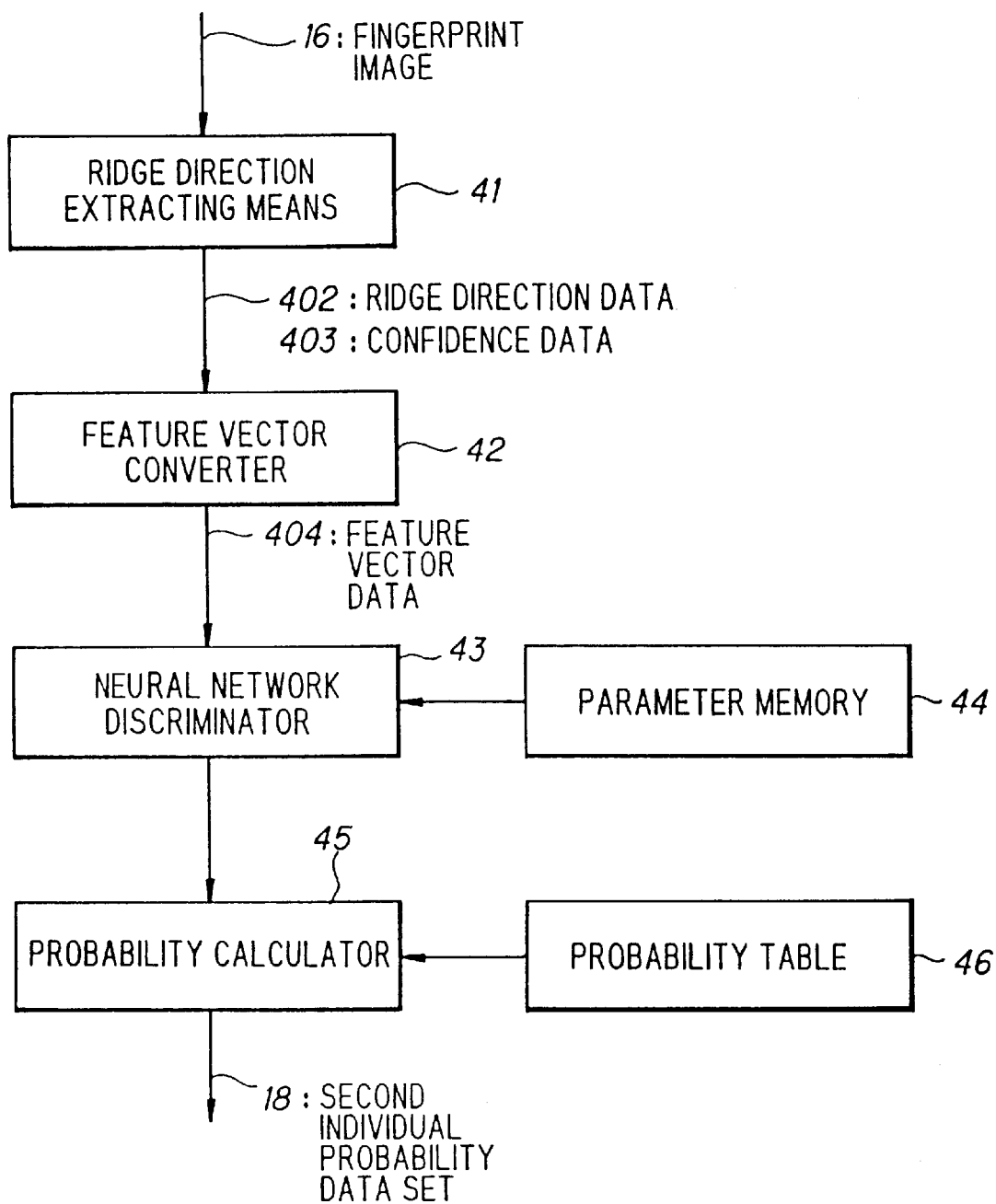
FIG. 13 is a block diagram illustrating an example of the second classification means 15 of FIG. 1.

FIG. 13 is a block diagram illustrating a basic composition of the classification means 15, comprising;

ridge direction extracting means 41 for extracting ridge directions and their confidence from the fingerprint image 16 supplied from the image input means 11 of FIG. 1 to be output as ridge direction data 402 and confidence data 403, a feature vector converter 42 for converting the ridge direction data 402 and the confidence data 403 into feature vector data 404, a neural network discriminator 43 for discriminating the fingerprint image 16 according to the feature vector data 404 delivered from the feature vector converter 42, a parameter memory 44 for storing parameters to be referred to by the neural network discriminator 43, and a probability calculator 45 for calculating each individual probability of the fingerprint image 16 to be classified into each of the five categories from output of the neural network discriminator 43 referring to a probability table 46, for outputting them as the second individual probability data set 18 of FIG. 1.

In the ridge direction extracting means 41, a ridge direction and a confidence of the ridge direction are extracted for each sub-region of the fingerprint image 16. As for the ridge direction extracting means 41, an apparatus described in a U.S. Pat. No. 5,717,786 entitled "Apparatus for Determining Ridge Direction Patterns" (hereafter called the fifth document) may be applied, for example.

In the following paragraphs, an example of the ridge direction extracting means 41 are described, wherein the apparatus of the fifth document is applied.

Figure 14:
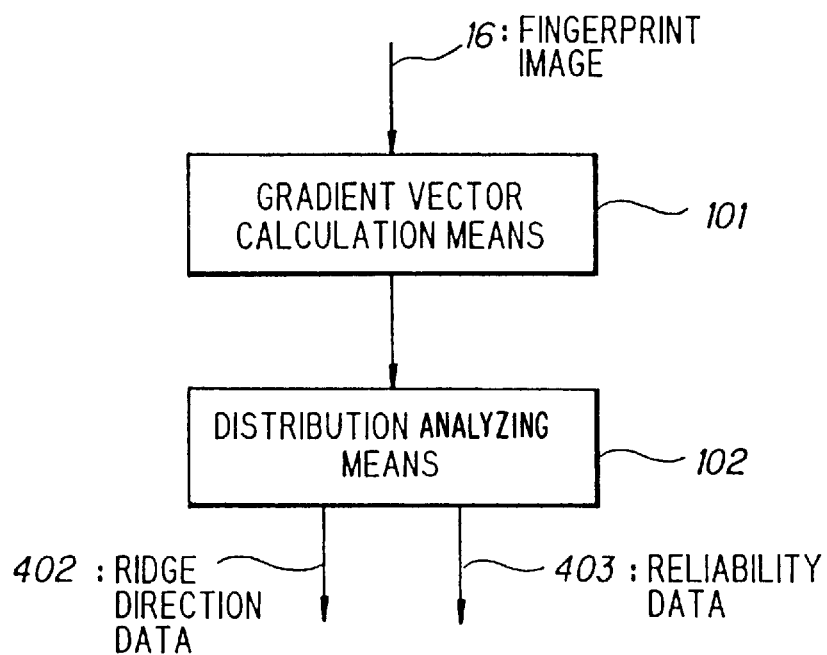
FIG. 14 is a block diagram illustrating the ridge direction extracting means 41 of FIG. 13.

FIG. 14 is a block diagram illustrating the ridge direction extracting means 41, provided with gradient vector calculation means 101 and distribution analyzing means 102.

Expressing the fingerprint image 16 having 512×512 pixels by a function $f(x,y)$, the gradient vector calculation means 101 calculates gradient vectors $\text{grad} f(x,y)=(f_x(x,y), f_y(x,y))$ for every coordinate $(x,y)$, $x$, $y$ being integers 1 to 512. Here, $$f_x(x, y) = \frac{\partial}{\partial x} f(x, y) \text{ and } f_y(x, y) = \frac{\partial}{\partial y} f(x, y).$$

These partial differentials can be obtained in practice from difference between two adjacent pixel values in x-direction and that in y-direction, respectively. The x and y components $f_x(x,y)$ and $f_y(x,y)$ of the gradient vectors $\text{grad} f(x,y)$ are delivered to the distribution analyzing means 102.

Figure 15:
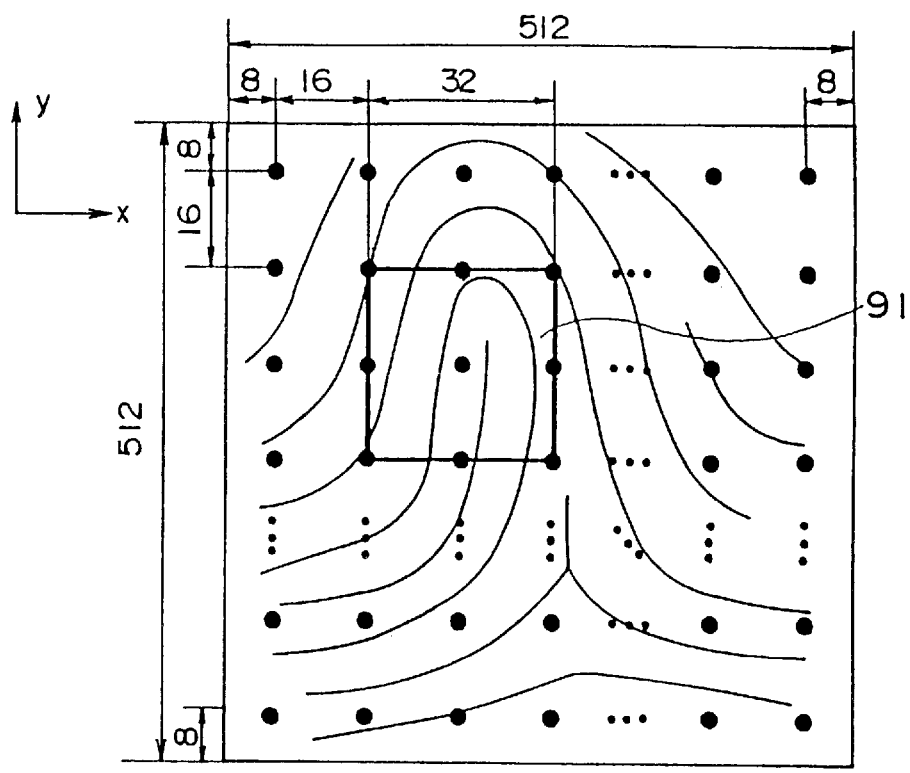
FIG. 15 illustrates one of 32×32 sub-regions, each sub-region being a region of 32×32 pixels half-overlapped with each adjacent sub-regions with its center ranged at every 16 pixels both in x and y directions of the fingerprint image 16 of 512×512 pixels.

The distribution analyzing means 102 calculates a ridge direction and its confidence, as follows, for each of 32×32 sub-regions, each sub-region being a region of 32×32 pixels half-overlapped with each adjacent sub-regions with its center ranged at every 16 pixels both in x and y directions of the fingerprint image 16 of 512×512 pixels as illustrated in FIG. 15.

Figure 16A:
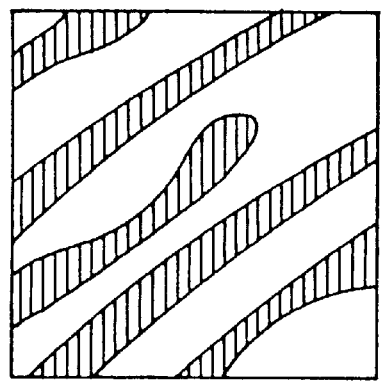
FIG. 16A illustrates an example of ridge line images in a sub-region.
Figure 16B:
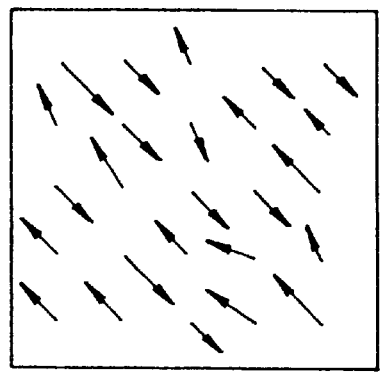
FIG. 16B shows gradient vectors at each coordinates of FIG. 16A.
Figure 16C:
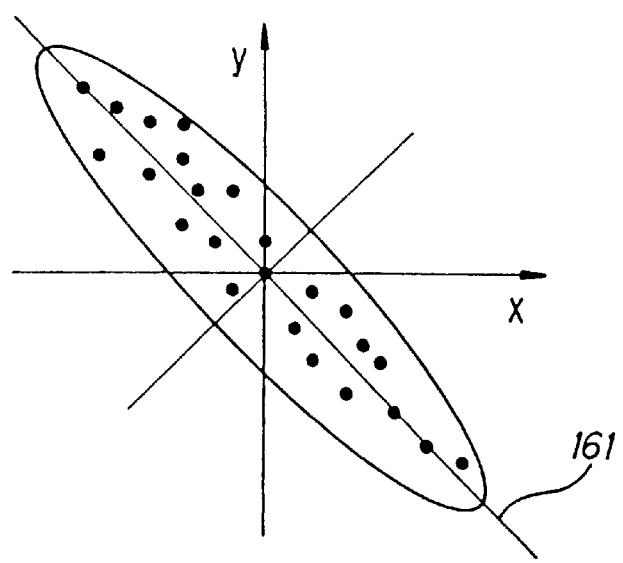
FIG. 16C is a graphic chart representing distribution of the gradient vectors of FIG. 16B.

FIG. 16A shows an example of the sub-region, of which the gradient vectors have their directions almost perpendicular to ridge lines as illustrated in FIG. 16B. FIG. 16C is a graphic chart representing distribution of the gradient vectors of FIG. 16B, wherein each of the gradient vectors is represented by a dot plotted on coordinates having values of its x and y components. As shown in FIG. 16C, the distribution of the gradient vectors has a principal axis 161 perpendicular to ridge lines in the sub-region. So, ridge direction of a sub-region can be calculated by analyzing gradient vector distribution of the sub-region.

In the gradient vector calculation means 102, the principal axis 161 is obtained by a principal component analysis, as follows.

When a sub-region is denoted by S, a variance-covariance matrix of gradient vectors in the sub-region S is expressed by following matrix V.

$$V = \begin{pmatrix} \sigma_{xx} & \sigma_{xy} \\ \sigma_{xy} & \sigma_{yy} \end{pmatrix},$$

where $$\sigma_{pq} = \frac{1}{N} \sum_{(x,y) \in S} (f_p(x, y) - \overline{f_p(x, y)})(f_q(x, y) - \overline{f_q(x, y)}),$$

N being number of gradient vectors in the sub-region S, and p, q being either x or y and $\bar{z}$ expressing average value of z.

Representing eigenvalues of the matrix V by $\lambda_1$ and $\lambda_2$ ($\lambda_1 > \lambda_2$) and their corresponding eigenvectors by $e_1$ and $e_2$, respectively, the eigenvector $e_2$ (the second axis) corresponding to the smaller eigenvalue $\lambda_2$ has its direction perpendicular to the principal axis (the first axis) of the distribution to be output as the ridge direction of the sub-region S.

Further, the larger eigenvalue $\lambda_1$ represents components of the gradient vectors in the sub-region S in the same direction of the eigenvector $e_1$. It means that the larger value of the eigenvalue $\lambda_1$ shows the clearer ridge line images without blot or scratch. Still further, in a sub-region including more noises, directions of the gradient vectors are more scattered, and so, difference between the eigenvalues $\lambda_1$ and $\lambda_2$ becomes less.

On these consideration, confidence r of the ridge direction is calculated according to the following equation in the example.

$$r = \sqrt{\lambda_1} - \sqrt{\lambda_2}$$

The confidence r represents reliability of the calculated ridge direction, showing a large value for a sub-region consisting of clear ridge line images with little noise, and a small value for that consisting of vague ridge line images with much noise.

Thus, the ridge direction extracting means 41 of FIG. 13 extract ridge direction data 402 and their confidence data 403 for each sub-region. In the following paragraphs, ridge direction of a sub-region at coordinates (m,n) (m, n=0, 1, ..., 31) is expressed by $\theta(m,n)$ ($\pi > \theta(m,n) > 0$) and its confidence by r(m,n).

Then the feature vector converter 42 of FIG. 13 converts ridge directions $\theta(m,n)$ and their confidences r(m,n) into a feature vector x according to the following equation.

$$x = \begin{pmatrix} x(0) \\ x(1) \\ \vdots \\ x(511) \end{pmatrix}$$

where, $$\begin{cases} x(16m/2 + n/2 + 0) = \dfrac{1}{4}\sum_{i=0}^{1}\sum_{j=0}^{1} r(m+i, n+j)\cos(2\theta(m+i, n+j)) \\ x(16m/2 + n/2 + 1) = \dfrac{1}{4}\sum_{i=0}^{1}\sum_{j=0}^{1} r(m+i, n+j)\sin(2\theta(m+i, n+j)) \end{cases}$$

m and n being even integers 0, 2, ..., 30.

The example of the above equation means that each component of 512-dimensional feature vector x is obtained by a mean value of x and y components of the ridge directions multiplied with their confidence, of adjacent four sub-regions.

The feature vector extracting means 42 may convert the ridge direction data 402 and the confidence data 403 into the feature vector data 404 in another way, according to the K-L (Karhuman-Loeve) development described in the fourth document by C. L. Wilson et al.

The feature vector data 404 thus obtained are processed for pattern discrimination by the neural network discriminator 43.

As for the neural network itself, there are published many documents, of which an example is "Neural Network Information Processing" by Aso, published by Sangyo-Tosho, 1988 (hereafter to be called the sixth document). Here, the neural network discriminator 43 is described in connection with a three-layered Perceptron neural network applied therein.

Figure 17:
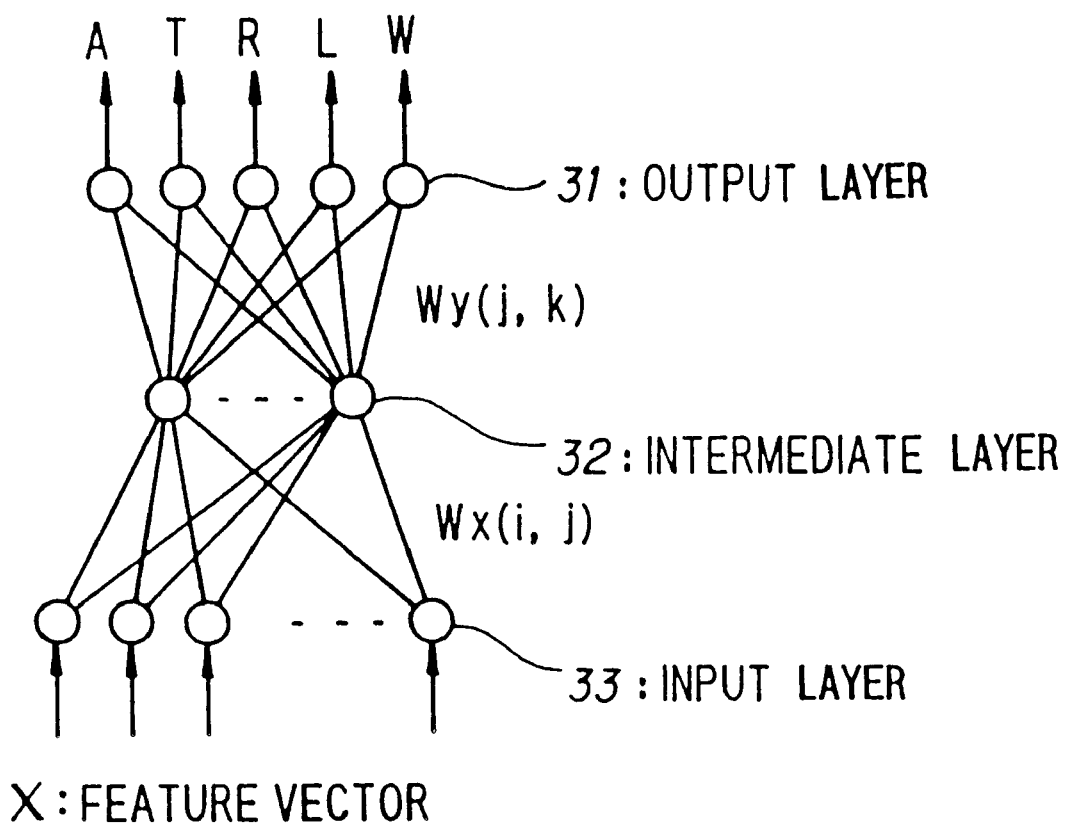
FIG. 17 is a model chart illustrating an example of a three layered Perceptron neural network, comprising an input layer 33, an intermediate layer 32 and an output layer 31.

FIG. 17 is a model chart illustrating an example of the three layered Perceptron neural network, comprising an input layer 33, an intermediate layer 32 and an output layer 31. In the example, the input layer 33 has $N_x=512$ units, the intermediate layer 32 has $N_y=20$ units and the output layer 31 has $N_z=5$ units, each unit of the output layer 31 corresponding to each of the five categories, the plain arch A, the tented arch T, the right loop R, the left loop L and the whorl W.

The $N_x$ (0 to $N_x-1$) units of the input layer 33 output, to each j-th unit (j=0 to $N_y-1$) of the intermediate layer 32, a value y(j) calculated from $N_x$ components x(i) (i=0 to $N_x$) of the feature vector x according to following equation, referring to parameters $w_x(i,j)$ and $t_x(j)$ which are prepared in the parameter memory 44 from teaching data set.

$$y(j) = f\left(\sum_{i=0}^{N_x-1} w_x(i,j)x(i) - t_x(j)\right),$$

where $f(\xi) = 1/(1+\exp(-\xi))$.

Similarly, the $N_y$ units of the intermediate layer 32 outputs a value z(k) of following equation to each k-th unit (k=0 to $N_z$) of the output layer 31 referring to parameters $w_y(j,k)$ and $t_y$ in the parameter memory 44 prepared from the teaching data set.

$$z(k) = f\left(\sum_{j=0}^{N_y-1} w_y(j,k)y(j) - t_y(k)\right),$$

where also $f(\xi) = 1/(1+\exp(-\xi))$.

The five output values z(k) thus calculated by the neural network discriminator 43, each having a value between 0 to 1 and corresponding to each of the five categories, are delivered to the probability calculator 45 of FIG. 13. In the following paragraphs, the five output values z(k) are represented by an output vector z expressed as follows.

$$z = \begin{pmatrix} z(A) \\ z(T) \\ z(R) \\ z(L) \\ z(W) \end{pmatrix} = \begin{pmatrix} z(0) \\ z(1) \\ z(2) \\ z(3) \\ z(4) \end{pmatrix}$$

Now, a method of preparing the parameters $w_x(i,j)$, $t_x(j)$, $w_y(j,k)$ and $t_y(k)$ in the parameter memory 44 is described.

As the teaching data set, certain number ($N_{train}$) of teaching feature vectors $x_m$ (m=0, 1, ..., $N_{train}$) are extracted from fingerprint images already classified into each category. For each of the teaching feature vectors $x_m$, its output vector $z_m$ is assigned, whereof a component corresponding to the category of the fingerprint is set to 1 and other components are set to 0. Following equation shows the output vector $z_m$ assigned for a teaching feature vector $x_m$ classified into the right loop R.

$$z = \begin{pmatrix} z(A) \\ z(T) \\ z(R) \\ z(L) \\ z(W) \end{pmatrix} = \begin{pmatrix} 0 \\ 0 \\ 1 \\ 0 \\ 0 \end{pmatrix}$$

With the teaching feature vectors $x_m$ and their output vectors $z_m$ thus prepared, the above parameters can be calculated, for example, by the "Error Back Propagation Algorithm" described pp. 50 to 54 of the sixth document by Aso et al.

The larger number being the better, teaching feature vectors of about 2,000 fingerprint images will give parameter values sufficiently practical for each category.

Returning to FIG. 13, the neural network discriminator 43 calculates the output vector z from the feature vector x of the fingerprint image 16, referring to the parameters thus prepared in the parameter memory 44.

Then, the probability calculator 45 calculates and outputs each individual probability of the fingerprint image 16 to be classified into each of the five categories, referring to values prepared in the probability table 46 corresponding to the output vector z.

Now, processes in the probability calculator 45 are described.

First, each component z(k) of the output vector z is quantized into one (s(k)) of three values according to following equation, for example.

$$s(k) = \begin{cases} 0 & \text{when } z(k) < \varepsilon_1 \\ 1 & \text{when } \varepsilon_1 \leq z(k) < \varepsilon_2 \\ 2 & \text{when } \varepsilon_2 \leq z(k) \end{cases}$$

As for the quantization levels $\varepsilon_1$ and $\varepsilon_2$, 0.1 and 0.9 may be applied, for example.

In the probability table 46, each one entry ($N_e$-th entry, $N_e$ represented by following equation, for example) is assigned for each ensemble of the quantized components s(k), or value of the quantized vector s. So, $243=3^5$ entries are assigned in the probability table 46 in case $N_z=5$, that is, the classification is performed into five categories.

$$N_e = \sum_{k=0}^{N_z} 3^k s(k)$$

In each of the entries of the probability table 46, probabilities to be classified into each category of a fingerprint image showing corresponding quantized vector s is registered, in a similar way with the probability table 983 of FIG. 11, as follows.

1) Another teaching data set is prepared from already classified fingerprint images different from those applied for preparing the parameters in the parameter memory 44.

2) For each fingerprint image of the teaching data set, processes in the ridge direction extracting means 41, the feature vector converter 42 and the neural network discriminator 43 are performed for obtaining entry number $N_e$ corresponding to its quantized vector s.

3) For each entry number $N_e$, each number $N_C$ of fingerprint images, classified into category C in the teaching data set and showing the entry number $N_e$, is counted for each category C.

4) From the numbers $N_C$ thus counted, probabilities $P_C$ to be registered in the $N_e$-th entry are calculated as $P_C = N_C / \Sigma_C N_C$.

In an example where there are 100 fingerprint images found to show the same entry number $N_e$=100, and 1, 2, 4, 3 and 90 of the 100 fingerprint images are originally classified into each of the five categories, the plain arch A, the tented arch T, the right loop R, the left loop L and the whorl W, respectively, following values are registered in the entry number 100.

$$\begin{pmatrix} P_A & = & 1/100 & = & 0.01 \\ P_T & = & 2/100 & = & 0.02 \\ P_R & = & 4/100 & = & 0.04 \\ P_L & = & 3/100 & = & 0.03 \\ P_W & = & 90/100 & = & 0.90 \end{pmatrix}$$

Referring to the probability table 46 thus prepared, the probability calculator 45 of FIG. 13 calculates and outputs the second individual probability data set 18 from the output vector z delivered through the neural network discriminator 43.

Thus, in the embodiment of FIG. 1 of the present invention, the first and the second individual data sets 17 and 18 are obtained to be supplied to the probability estimation means 13.

Now, another embodiment of the invention will be described in the following paragraphs referring to FIG. 18, wherein comprised;

image input means 11 for generating a fingerprint image 16, classification means 22 for performing fingerprint classification several ($N_p$) times in different way and generating several ($N_p$) individual probability data sets 27 indicating each individual probabilities of the fingerprint image 16 to be classified into each classification category, according to parameters designated by control means 24, probability estimation means 23 for calculating an integrated probability data set 19 from the several ($N_p$) individual probability data sets 27, and category decision means 14 for deciding and outputting a category or categories as a final classification result of the fingerprint image 16 according to the integrated probability data set 19.

Figure 18:
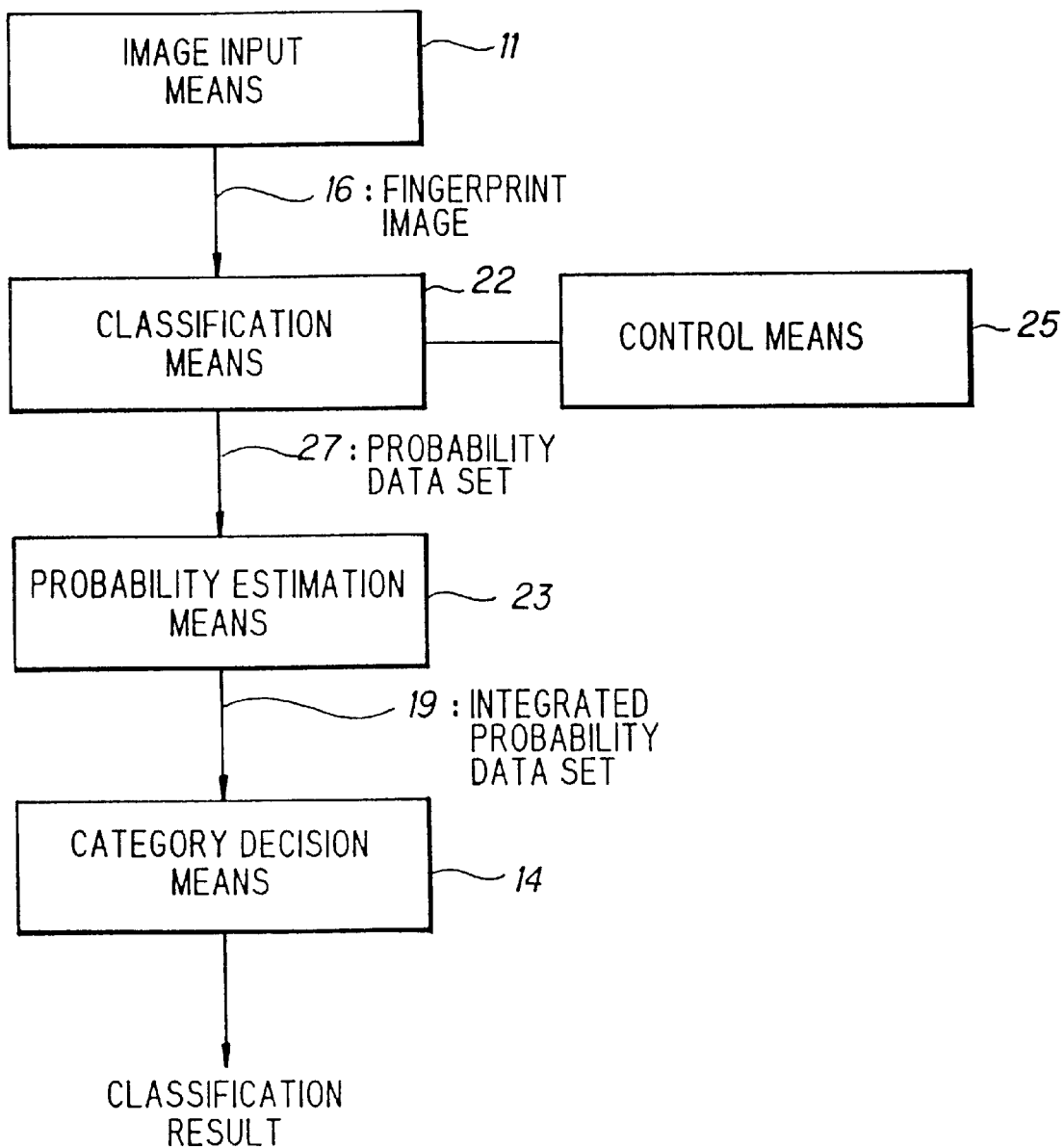
FIG. 18 is a block diagram illustrating another embodiment of fingerprint classification system of the invention.

In the same way with the embodiment of FIG. 1, a fingerprint image is generated by the image input means 11 of FIG. 18 and supplied to the classification means 22.

Figure 19:
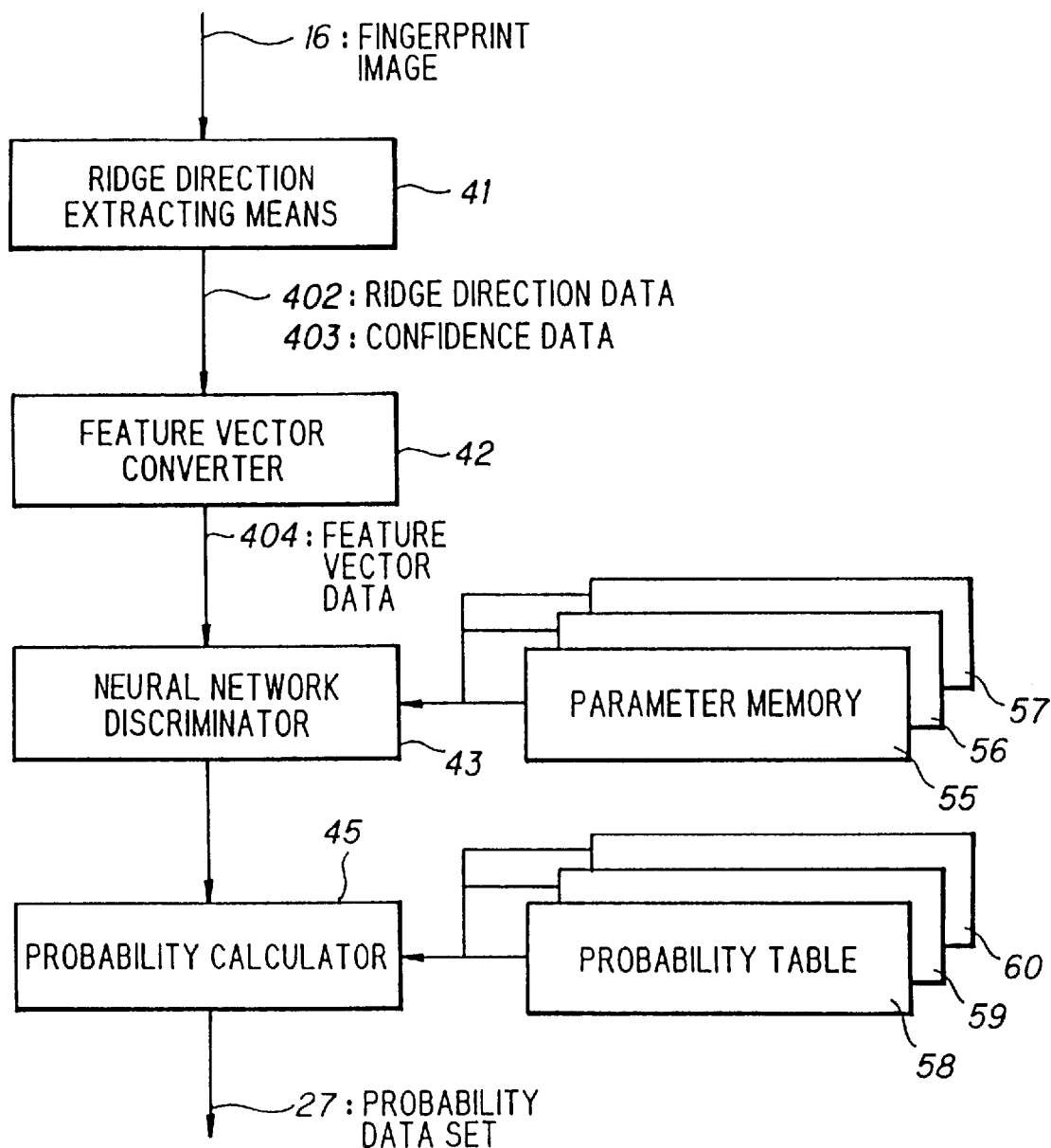
FIG. 19 is a block diagram illustrating configuration of the classification means 22 of FIG. 18.

As for the classification means 22 of FIG. 18, classification means illustrated in FIG. 19, making use of a neural network, is applied for example, having a similar configuration to the second classification means 15 illustrated in FIG. 15. The classification means 22 is provided with a plurality of (three in the example) parameter memories 55 to 57 and the same number of probability tables 58 to 60, different from the second classification means 15 illustrated in FIG. 13.

The same processes are performed in the ridge direction extracting means 41 and the feature vector converter 42, and duplicated descriptions are omitted.

In the network discriminator 43, an output vector z is similarly calculated for the same fingerprint image 16 applying parameter values prepared in each of the plurality of parameter memories 55 to 57 in the embodiment, according to a control signal delivered from the control means 25 of FIG. 18.

The probability calculator 45 calculates an individual probability data set 27 for each of the output vectors z referring to each corresponding probability table 58 to 60 according to the control signal delivered from the control means 25.

The parameter values of each of the parameter memories 55 to 57 are prepared from each different teaching data set in the same way with those of the parameter memory 44 of FIG. 13. Each of the probability tables 58 to 60 is then prepared corresponding to parameters in each of the parameter memories 55 to 57 applying each different teaching data set.

Thus, in the embodiment of FIG. 18, a plurality of ($N_p$=3 in the example) individual probability data sets 27 are obtained for the estimation in the probability estimation means 23.

The probability estimation means 23 estimate the integrated probability data set 19 indicating each integrated probability $P_0(C)$ of the fingerprint image 16 to be classified into each category C to be delivered to the category decision means 14, from the individual probabilities $P_i(C)$ (i=1, 2, ..., $N_p$) of the plurality of individual probability data sets 27, by the following arithmetic mean calculation, for example.

$$P_0(C) = \frac{1}{N} \sum_{i=0}^{N_P} P_i(C)$$

Thus, a fingerprint classification system for classifying fingerprint images is provided in the invention with a high precision by integrating merits of different classification means or different classification parameters efficiently, enabling an easy setting of its rejection level at the same time.

What is claimed is:

1. A fingerprint image classification system, comprising:
   a first classification unit configured to receive an input fingerprint image and to classify the input fingerprint image according to a first classification, the first classification unit outputting a first classification result that corresponds to a first set of probabilities;
   a second classification unit configured to receive the input fingerprint image and to classify the input fingerprint image according to a second classification different from the first classification, the second classification unit outputting a second classification result that corresponds to a second set of probabilities;
   a probability estimation unit configured to receive the first and second classification results from the first and second classification units, respectively, and to determine and output an integrated set of probabilities based on the first and second classification results; and
   a category decision unit configured to receive the integrated set of probabilities and to determine a greatest probability in said integrated set of probabilities, the greatest probability in said integrated set of probabilities corresponding to a particular fingerprint category that is output as a classification result for the input fingerprint image,
   wherein the category decision unit outputs at least two classification results based on the corresponding classification result for the greatest probability in said integrated set of probabilities and the corresponding classification result for a next-greatest probability in said integrated set of probabilities, and
   wherein the at least two classification results are output as a set of classifications for the input fingerprint image only if a sum of the greatest probability and the next-greatest probability is greater than a predetermined threshold value.

2. A fingerprint image classification method, comprising:
   receiving an input fingerprint image;
   classifying the input fingerprint image according to a first classification, and outputting a first classification result that corresponds to a first set of probabilities;
   classifying the input fingerprint image according to a second classification different from the first classification, and outputting a second classification result that corresponds to a second set of probabilities;
   determining an integrated set of probabilities based on the first and second classification results; and
   determining a greatest probability in said integrated set of probabilities, the greatest probability in said integrated set of probabilities corresponding to a particular fingerprint category that is output as a classification result for the input fingerprint image,
   wherein at least two classifications are output as the classification result for the input fingerprint image, one of the two classifications being the corresponding classification result for the greatest probability in said integrated set of probabilities, and another of the two classifications being the corresponding classification result for a next-greatest probability in said integrated set of probabilities, and
   wherein the at least two classification results are output as a set of classifications for the input fingerprint image only if a sum of the greatest probability and the next-greatest probability is greater than a threshold value.

* * * * *